United States Patent [19]

Namekawa et al.

[11] Patent Number: 4,651,745
[45] Date of Patent: Mar. 24, 1987

[54] ULTRASONIC DOPPLER DIAGNOSTIC DEVICE

[75] Inventors: Kouroku Namekawa; Akimitsu Harada, both of Tokyo, Japan

[73] Assignee: Aloka Co., Ltd., Tokyo, Japan

[21] Appl. No.: 717,494

[22] Filed: Mar. 28, 1985

[30] Foreign Application Priority Data

Apr. 2, 1984 [JP] Japan ............................... 59-063283

[51] Int. Cl.$^4$ ............................................. A61B 10/00
[52] U.S. Cl. .................................. 128/663; 73/861.25
[58] Field of Search ....................... 128/663; 73/861.25

[56] References Cited

U.S. PATENT DOCUMENTS 4,095,597 6/1978 Hassler ................................. 128/663

Primary Examiner—Edward M. Coven
Assistant Examiner—Francis J. Jaworski
Attorney, Agent, or Firm—Koda and Androlia

[57] ABSTRACT

An ultrasonic diagnostic device for measuring the velocity of blood flow within a living body comprises a transmitter for transmitting an ultrasonic wave into the body, a receiver for amplifying the part of the ultrasonic wave reflected from the body, converting it into an electric signal and amplifying the signal in accordance with a logarithmic amplification characteristic, a converter circuit which receives the amplified signal from the receiver and a reference signal from the transmitter and outputs a signal corresponding to the ratio of the component of the reflected ultrasonic wave attributable to the blood flow and the component thereof attributable to the wall of the blood vessel through which the blood flows, an extraction circuit which receives the amplified signal from the receiver and outputs a signal corresponding to the component attributable to the wall of the blood vessel, and an arithmetic circuit which multiplies the signals output by the converter circuit and the extraction circuit, whereby there is obtained a signal corresponding to the velocity of the blood flow.

1 Claim, 1 Drawing Figure

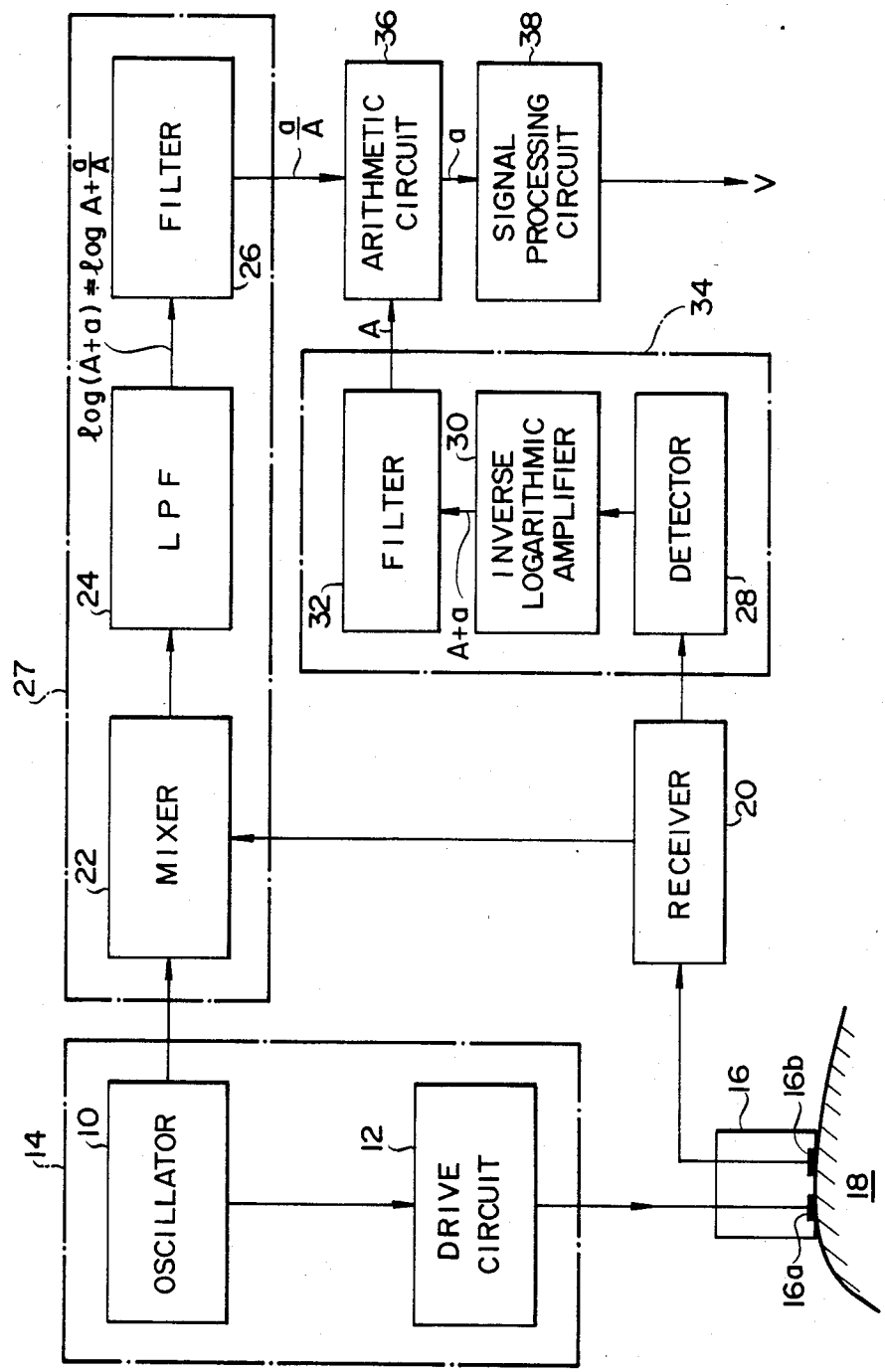

ULTRASONIC DOPPLER DIAGNOSTIC DEVICE

BACKGROUND OF THE INVENTION

1. Field of the Invention

This invention relates to an ultrasonic Doppler diagnostic device, more particularly to an improved ultrasonic Doppler diagnostic device for detecting blood flow within a living organism or for measuring the velocity or the amount of such blood flow.

2. Description of the Prior Art

The ultrasonic Doppler method is widely used for noninvasively detecting and measuring the movement of a moving member within a living organism and, specifically, is commonly used for noninvasive detection and measurement of blood flow within the heart, blood vessels etc.

Generally speaking, however, the ultrasonic wave reflected from the blood flow is mixed together with an ultrasonic wave component reflected by the wall of the blood vessel or the heart which surrounds the blood flow (such component being referred to as the "wall signal" hereinafter). This is particularly troublesome since the the blood flow signal is much weaker than the wall signal.

Although the amplitude of the wall signal can be reduced by focusing the ultrasonic wave into a fine beam, there is a limit to how sharply the beam can be focused so that even when this method is used the reflected wave nevertheless includes a high-level wall signal along with a low-level blood flow signal. As a result, there has been the disadvantage that the strong wall signal makes it difficult to obtain the desired blood flow signal.

Conventionally, the separation of the blood flow signal from the wall signal has been carried out on the basis of frequency difference. This is possible since the wall signal is a wave reflected from a substantially non-moving portion so that its frequency following comparison with the reference wave according to the Doppler method is relatively low, whereas the corresponding frequency for the wave reflected from the moving blood is, because of the Doppler effect, relatively high. This frequency difference can be used to separate the two signals. More specifically, by passing the mixed signals through a filter, the strong but low frequency wall signal can be separated from the weaker, higher frequency blood flow signal.

Nevertheless, conventional devices operating on this principle have not been able to produce the desired results when the detection or measurement is carried out for blood flow within very fine blood vessels. This is because in such cases the ratio of the wall signal to the blood flow signal becomes extremely large so that when the blood flow signal is amplified by a degree adequate to make it detectable, the wall signal, which is amplified by the same degree, becomes so large as to saturate the receiver circuit. As a consequence, it becomes difficult, if not impossible, to detect the blood flow signal.

SUMMARY OF THE INVENTION

In view of the above-mentioned disadvantages inherent in conventional apparatuses, it is the object of the present invention to provide an improved ultrasonic Doppler diagnostic device which can effectively detect blood flow within fine blood vessels or in regions near the heart wall.

In order to attain this object, the present invention provides an ultrasonic Doppler diagnostic device for detecting or measuring blood flow by use of the Doppler effect, said ultrasonic Doppler diagnostic device comprising a converter circuit for obtaining the ratio between the wall signal and the blood flow signal in the received wave, an extraction circuit for extracting the wall signal from the received wave, and an arithmetic circuit for multiplying the outputs from the the converter circuit and the extraction circuit to eliminate the wall signal and obtain only the blood flow signal as output.

BRIEF EXPLANATION OF THE DRAWING

The FIGURE shows a block circuit diagram of one embodiment of the ultrasonic Doppler diagnostic device according to the invention.

DESCRIPTION OF THE PREFERRED EMBODIMENT

Referring to the FIGURE, an oscillator 10 produces a stable high frequency signal which is passed through a drive circuit 12 and used to drive a piezoelectric transmitter element 16a of a probe 16. The oscillator 10 and the drive circuit 12 together constitute a transmitter 14. As a result, an ultrasonic wave is radiated from the piezoelectric transmitter element 16a toward a living organism 18 and upon entering the organism 18 is partially reflected. The reflected wave is picked up by a piezoelectric receiver element 16b provided in the probe 16 and is converted into an electric signal.

The electric signal produced from the reflected wave is amplified by a receiver 20, which in accordance with one feature of the present invention carries out logarithmic amplification.

For the reason mentioned earlier, the electric signal received by the receiver 20 from the piezoelectric receiver element 16b includes a large wall signal of high output level together with a weak blood flow signal. If this composite signal should be amplified by an amplifier with an ordinary amplification characteristic, the amplifier would reach saturation because of the large ratio between the wall signal and the blood flow signal. As a result, it would be difficult to detect the weak blood flow signal. Moreover, this difficulty would increase in proportion to decreasing size of the blood vessel since the smaller is the blood vessel the greater is the disparity between the strengths of the wall signal and the blood flow signal.

Therefore, as stated above, in the present invention the receiver 20 is designed to amplify according to a logarithmic amplification characteristic so as to prevent saturation and make it possible to detect the weak blood flow signal.

The receiver 20 can be easily constituted to exhibit a logarithmic amplification characteristic by using a conventional logarithmic amplifier, an amplifier provided with an automatic gain control circuit, or the like.

The output from the receiver 20 is supplied to a mixer 22 which also receives the signal output by the oscillator 10. The two signals are mixed and detected in the mixer 22, with the signal from the oscillator 10 being used as the reference signal.

The output from the mixer is forwarded to a low-pass filter 24 which passes only the difference frequency obtained by mixing the two frequencies in the mixer 22 so that the output from the low-pass filter constitutes a frequency shift signal resulting from the comparison of the two signals. It must be noted, however, that this frequency shift signal includes both a large, low-frequency signal component attributable to the slow movement of the blood vessel wall, heart wall etc. and a small, high-frequency blood flow signal component attributable to the blood flow. It is of course necessary to separate out the blood flow signal component.

One feature that characterizes the present invention is the effective use made of the logarithmic amplification characteristic of the receiver 20 for separating the wall signal and blood flow signal components. The separation in accordance with this feature is carried out by a converter circuit 27 constituted of the mixer 22, the low-pass filter 24 and a filter 26. The function of the converter circuit 27 is to obtain the ratio between the blood flow signal component and the wall signal component. More specifically, if the amplitude of the blood flow signal component of the received wave is denoted as a and that of the wall signal component is denoted as A, then the output obtained after logarithmic amplification in the receiver 20, comparison with the reference wave in the mixer 22 and removal of the high-frequency component by the low-pass filter 24 can be represented as:

$$\log (A+a) = \log A (1+a/A) \simeq \log A + a/A$$

The first term of the aforesaid equation ($\log A$) is thereafter removed by passing the output from the low-pass filter 24 through the filter 26, which is a high-pass filter or a band-pass filter capable of removing only the first term ($\log A$) constituted of a low-frequency component attributable to the wall signal A. As a result, the output from the filter 26 approximates the value $a/A$.

From this it will be understood that from the converter circuit 27 it is possible to obtain the ratio between the blood flow signal a and the wall signal A.

The received wave signal from the receiver 20 is also supplied to an extraction circuit 34 which, being constituted of a detector 28, an inverse logarithmic amplifier 30 and a filter 32, is capable of extracting the wall signal A from the received wave.

More precisely, the detector 28 detects the envelope of the signal constituted by the received wave output by the receiver 20, whereafter this envelope is processed by the inverse logarithmic amplifier 30, which is arranged to have the opposite amplification characteristic from the receiver 20.

As the inverse logarithmic amplifier 30 of this embodiment there may be used, for example, an amplifier having a feedback circuit with an inverse logarithmic characteristic or a conventional antilog circuit.

It is therefore obvious that the output from the inverse logarithmic amplifier 30 will be $A+a \simeq A$. Moreover, as this received wave signal which is now non-logarithmic in nature is passed through the filter 32 to have its low-frequency component removed, it will be seen that the output of the extraction circuit 34 is the wall signal A.

The output a/A from the converter circuit 27 and the output A from the extraction circuit 34 are both forwarded to an arithmetic circuit 36 where they are multiplied. As a result of this multiplication, the arithmetic circuit 36 outputs effectively only the blood flow signal a without saturating the receiver even in the case of existing strong wall signals.

The calculated blood flow signal a is sent to a signal processing circuit 38 which converts it into a velocity signal v. It is thus possible to know the blood flow velocity.

On the other hand, in cases where the wall signal A is adequately small in comparison with the blood flow signal a, it is possible to omit the inverse logarithmic amplifier 30 from the extraction circuit 34.

Further, although the embodiment described above relates to a continuous type Doppler device, the invention can also be applied to a conventional pulse type Doppler device or to a secondary Doppler device of either type.

As was explained in the foregoing, in accordance with the present invention, logarithmic amplification is carried out in a receiver, the ratio of the blood flow signal to the wall signal and the wall signal alone are respectively derived from the received wave signal, and the so-obtained ratio and wall signal are multiplied to obtain the blood flow signal separately from the wall signal without saturating the receiver. As a result, measurement of blood flow velocity can be easily and accurately carried out even in respect of very small diameter blood vessels.

We claim:

1. In an ultrasonic Doppler diagnostic device which radiates an ultrasonic wave into a living organism, receives a reflected wave from the organism and detects the frequency shift of the received wave by comparing it with a reference wave, the improved ultrasonic Doppler diagnostic device comprising a receiver for amplifying the received wave in accordance with a logarithmic amplification characteristic, an extraction circuit for removing from the received wave the amplitude of the wall signal attributable to the wall of the blood vessel or the like through which the blood flows, a converter circuit for converting the received wave into the ratio of the blood flow signal to the wall signal, and an arithmetic circuit for multiplying the outputs of the extraction circuit and the converter circuit and outputting only the blood flow signal.

* * * * *